US00PP35414P2

(12) United States Plant Patent
Dibley

(10) Patent No.: US PP35,414 P2
(45) Date of Patent: Oct. 3, 2023

(54) ***BEGONIA* PLANT NAMED 'BBEN033-0'**

(50) Latin Name: *Begonia rex-cultorum*
Varietal Denomination: BBEN033-0

(71) Applicant: Dibley's Nurseries, Ruthin (GB)

(72) Inventor: Lynne Dibley, Ruthin (GB)

( * ) Notice: Subject to any disclaimer, the term of this patent is extended or adjusted under 35 U.S.C. 154(b) by 0 days.

(21) Appl. No.: 18/103,504

(22) Filed: Jan. 31, 2023

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./263.1, 343
See application file for complete search history.

*Primary Examiner* — Karen M Redden
(74) *Attorney, Agent, or Firm* — Cassandra Bright

(57) ABSTRACT

A new and distinct variety of *Begonia rex-cultorum* plant named 'BBEN033-0' is disclosed, characterized by a large palmate foliage. Plants have silver foliage with a dark pink center and distinctive very dark greyed-purple to black margin. Plants are large, upright and grow rapidly. The new variety is a *Begonia*, normally used as an ornamental garden or container plant.

1 Drawing Sheet

Latin name of the genus and species: *Begonia rex-cultorum.*

Variety denomination: 'BBEN033-0'.

BACKGROUND OF THE INVENTION

The new cultivar is the product of a planned breeding program. The new variety originated as the result of a cross performed during 2018 of an unnamed, unpatented proprietary *Begonia rex-cultorum* as the seed parent, and the unpatented *Begonia rex-cultorum* 'Midnight Magic' as the pollen parent. The selection of the new variety was made during August of 2018 by the inventor at a research greenhouse located in Wales, UK.

Asexual reproduction of the new cultivar 'BBEN033-0' was first performed at a research greenhouse located in Wales, UK by terminal vegetative cuttings in August of 2018. 'BBEN033-0' has since produced three generations by vegetative cuttings and has shown that the unique features of this cultivar are stable and reproduced true to type.

SUMMARY OF THE INVENTION

The cultivar 'BBEN033-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BBEN033-0'. These characteristics in combination distinguish 'BBEN033-0' as a new and distinct *Begonia rex-cultorum* cultivar:

1. Upright plant habit.
2. Palmate leaf.
3. Rapid growth.
4. Large plant.
5. Silver foliage with a dark pink center and distinctive very dark greyed-purple to black margin.

PARENT COMPARISON

Plants of the new cultivar 'BBEN033-0' are similar to plants of the seed parent variety in most horticultural characteristics. However, plants of the new cultivar 'BBEN033-0' differ in the following:

1. Leaves of the new variety are larger than leaves of the seed parent.
2. Plants of the new variety have a shorter, less leggy habit than the seed parent.
3. Plants of the new variety grow faster than plants of the seed parent.
4. Plants of the new variety have shorter internodes than the seed parent plant.
5. Foliage of the new variety has a pink center and dark margins not found on the seed parent.

Plants of the new cultivar 'BBEN033-0' are similar to plants of the pollen parent variety in most horticultural characteristics. However, plants of the new cultivar 'BBEN033-0' differ in the following:

1. Leaves of the new variety are palmate, leaves of the pollen parent are cordate.
2. Plants of the new variety are taller than plants of the pollen parent.
3. Foliage of the new variety is silver with a dark pink heart and very dark purple to black margin, foliage of the seed parent is dark green.
4. Plants of the new variety are not as susceptible to fungal infection as are plants of the pollen parent.
5. Foliage of the new variety is not as deeply rugose as foliage of the pollen parent.

COMMERCIAL COMPARISON

Plants of the new cultivar 'BBEN033-0' are similar to plants of the commercial variety, *Begonia* 'BDIBL12-0' U.S. Plant Pat. No. 33,502 in most horticultural characteristics including plant habit and leaf shape. Foliage color of the new cultivar 'BBEN033-0' differs in the following:

1. Foliage of the new variety has a silver background, distinctive dark pink center and very dark purple to black margin. Foliage color of 'BDIBL12-0' has a distinct lavender pater than becomes more vivid and darker towards the center.

Plants of the new cultivar 'BBEN033-0' are similar to plants of the commercial variety, *Begonia* 'BRXBR15-0' U.S. Plant Pat. No. 24,110 in most horticultural characteristics. Plants of the new cultivar 'BBBEN033-0' differ in the following:

1. Foliage of the new variety has a jagged margin not found on 'BRXBR15-0'.
2. Foliage of the new variety is silver with a dark pink center and very dark purple to black margin; foliage of 'BRXBR15-0' is red with black margins.
3. Plants of the new variety are shorter than plants of this comparator.

BRIEF DESCRIPTION OF THE PHOTOGRAPH

The present invention of a new and distinct variety of *Begonia* is shown in the accompanying photograph, the colors being as nearly true as possible with color photographs of this type. The accompanying figure illustrates a typical plant of 'BBEN033-0'. Age of the plant is approximately 16 weeks, shown in a 1 gallon pot.

DETAILED BOTANICAL DESCRIPTION

In the following description, color references are made to The Royal Horticultural Society Colour Chart 2007 except where general terms of ordinary dictionary significance are used. The following observations and measurements describe 'BBEN033-0' plants grown in a commercial controlled greenhouse in Somis, Calif. Measurements and numerical values represent averages of typical plant types.

Botanical classification: *Begonia rex-cultorum* 'BBEN033-0'.

Age of plant described: Approximately 16 weeks.

Container of plant described: 1-gallon pot.

PROPAGATION

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with The R.H.S. Chart.

PLANT

Growth habit: Upright growing, fleshy annual.

Plant shape: Upright, flattened globular.

Pot size of plant described: 1 gallon.

Height: Approximately 40 cm.

Plant spread: Approximately 55 cm.

Growth rate: Rapid.

Branching characteristics: Basally emerging foliage, no actual branches, only petioles.

Foliage:

*Type*.—Single, basally emerging foliage and long petioles.

*Orientation*.—Mainly upwardly facing foliage. Lower, oldest foliage outwardly facing.

*Strength*.—Very strong, hard foliage, resists breakage.

*Texture, top surface*.—Leathery, slightly rugose along main vein. Moderately hirsute throughout blade.

*Texture lower surface*.—Main surface non-pubescent, veins sparsely hirsute. Largest veins more densely hirsute.

*Appearance*.—Metallic, matte and slightly leathery appearance to upper surface. Lower surface matte.

*Quantity*.—Approximately 22 to 30.

*Shape of blade*.—Overall palmate.

*Apex*.—Acute.

*Base*.—Cordate, non-overlapping very slightly overlapping top of leaf surface.

*Margin*.—Incised and serrate. Sinuses acute, average depth approximately 0.8 to 1.8 cm.

*Aspect*.—Flat.

*Mature leaves*.—

*Average length*.—Average range 12 to 18 cm.

*Average width*.—Average range 12 to 16 cm.

*Color*.—Mature foliage upper side: Main color near Greyed-Green 188C with sheen near 191D. Center blotch, approximately 20% of leaf blade near Red-Purple 64A, with Greyed-Purple N187A feathering around veins near center. Feathering near lateral veins about 30% from margin colored near Greyed-Green N189A. Well defined margin colored near Greyed-Purple N187A and Black 202A. Mature foliage under side: Main color near Greyed-Green 188C flushed Red-Purple 59C. Center blotch, approximately 20% of leaf blade RHS Greyed-Purple 187B flushed Red-Purple 64A. Well defined margin colored near Greyed-Purple 187A and Black 202A. Venation: Type: Palmate. Venation color upper side: Center venation colored near Red-Purple N57C. About halfway to apex veins are colored near 59B. Venation color under side: Near Red-Purple 59A.

*Petiole*.—Length: Average range 14 to 18 cm. Diameter: Approximately 8 to * mm. Color: Background color near RHS Greyed-Purple 185C, flushed Red-Purple 58A. Texture: Hirsute.

*Stipule description*.—Length: Approximately 1.3 cm. Diameter: Approximately 1.0 cm. Shape: Deltate. Apex: Acute. Base: Truncate. Color: Immature near RHS Greyed-Purple 187C flushed 58A, upper and lower surfaces. Dries to Brown 200D, upper and lower surfaces, before leaf matures. Texture: Upper Surface: Very sparsely pilose. Lower Surface: Glabrous.

Flower: Not observed to date.

Reproductive organs: Not observed to date.

OTHER CHARACTERISTICS

Seeds and fruits: Not observed to date.

Disease/pest resistance: The new variety shows some increased resistance to fungal diseases of *Begonia*. Typical fungal diseases include *Xanthomonas, Botrytis, Odium* and *Pythium*. Neither resistance nor susceptibility to other diseases or pests of *Begonia* has been observed in this variety.

Temperature tolerance: The new variety tolerates temperatures from approximately 5° to 35° C.

What is claimed is:

1. A new and distinct cultivar of *Begonia rex-cultorum* plant named 'BBEN033-0' as herein illustrated and described.

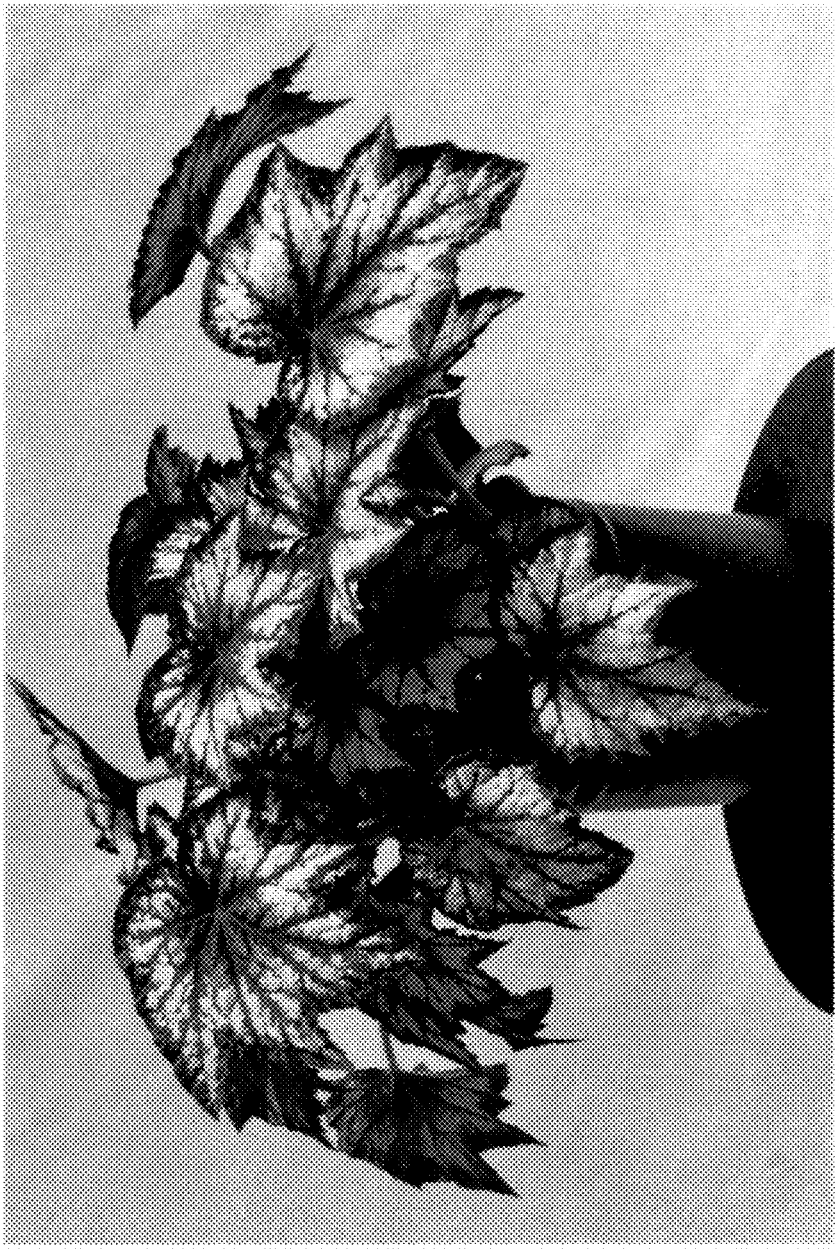

* * * * *